United States Patent [19]

Raemer et al.

[11] 4,233,842
[45] Nov. 18, 1980

[54] APPARATUS FOR MEASUREMENT OF EXPIRATION FLUIDS

[75] Inventors: Daniel B. Raemer; Dietrich K. Gehmlich; Dwayne R. Westenskow, all of Salt Lake City, Utah

[73] Assignee: University of Utah, Salt Lake City, Utah

[21] Appl. No.: 953,234

[22] Filed: Oct. 20, 1978

[51] Int. Cl.³ ............................ G01F 1/00; A61B 5/08
[52] U.S. Cl. ................................. 73/861.04; 128/725; 128/719
[58] Field of Search ............ 73/194 R, 194 E, 194 M, 73/23; 128/2.07, 2.08

[56] References Cited

U.S. PATENT DOCUMENTS

| | | | |
|---|---|---|---|
| 1,988,221 | 1/1935 | Soskin | 128/2.07 |
| 2,630,798 | 3/1953 | White et al. | 128/2.07 |

*Primary Examiner*—Herbert Goldstein
*Attorney, Agent, or Firm*—Thorpe, North & Gold

[57] ABSTRACT

A dynamic method and apparatus for determining the rate of expiration of a selected fluid constituent expired by a living subject during respiration. The apparatus includes a fluid path system which conducts the expired air to a first fluid detector which produces a first signal operable as a function of concentration for the selected fluid constituent. The signal registered by the detector is used for later comparison with a second signal which provides the basis for determining the expiration rate of fluid constituent originally present in the expired air. To make this determination, the fluid constituent is removed from the expired air, with the expired air being advanced to a mixing chamber where a second detection means senses the fluid concentration. The respective signals from the first and second detection means are compared and integrated and additional fluid constituent is added to the expired air at the mixing chamber by a metering pump until the respective signals are equal, indicating equivalent concentrations. Since the flow rate of fluid constituent replenished is a function of rate of expiration for the selected fluid constituent, this value can be used to obtain the value of the latter. Such a system can be readily adapted to existing anesthesia delivery systems, as well as other respiratory monitoring apparatus. Fluids which are subject to measurement by such a method and apparatus include $CO_2$, anesthetics, alcohols, water vapor and numerous gases.

16 Claims, 2 Drawing Figures

APPARATUS FOR MEASUREMENT OF EXPIRATION FLUIDS

BACKGROUND OF THE INVENTION

1. Field of Invention

This invention relates to the detection and measurement of selected fluids present in expired air associated with the respiration of a living subject. More specifically, the invention pertains to determination of expiration rates or concentration of a selected fluid constituent in a fraction of expired air taken from a living subject during respiration.

2. Description of Prior Art

The detection and measurement of various fluids constituents present in the expired air of a living subject can provide valuable information with regard to numerous physiological processes in addition to respiratory functions. Values for oxygen consumption rate ($\dot{V}O_2$) and $CO_2$ production rate ($\dot{V}CO_2$) serve as timely indicators of relative changes in cardiovascular function and tissue perfusion in critically-ill patients. Such values also provide the basis for calculation of metabolic rate, a parameter which is particularly significant in burn patients whose metabolic rate may increase by fifty to three hundred percent. Such patients must be closely monitored in view of the common increase of catbolism of protein and associated loss of body weight resulting from the break down of tissue required to supply energy for such dramatic metabolic requirements. Furthermore, $\dot{V}O_2$ and $\dot{V}CO_2$ values are useful in the calculation of energy expenditure for a patient in connection with surgery, infection or injury. An awareness of metabolic rate can provide an accurate basis for dietary planning to insure that calorie intake is properly coordinated to avoid lipogenesis or other adverse physiological consequences of excess calorie consumption.

Although instrumentation is available to obtain $\dot{V}O_2$ and $\dot{V}CO_2$ measurements, such instrumentation is typically complex and expensive. Current apparatus for monitoring $\dot{V}CO_2$, for example, generally utilizes a programmable calculator or computer, a flow metering device (ultrasonic, turbine, differential pressure, oscillating bellows) and an infrared gas analyzer, a mass spectrometer or a gas chromatograph. In such a system, the expired gases are either collected in a spirometer or are passed through a flow meter and integrated electronically to obtain an exhaled minute volume.

The $CO_2$ concentration of the exhaled volume is measured with one of the aforementioned $CO_2$ sensors and $\dot{V}CO_2$ is accordingly calculated. Such systems are not only extremely expensive, but are cumbersome to move and require expert attendance for accurate operation. Part of the cause for such complexity and expense arises from the approach by such prior art systems to make direct quantitative measurement of the $CO_2$ fluid constituent. Such direct measurement have not only resulted in complex and expensive $CO_2$ measurement devices, but have tended to limit progress in the art of detection and quantitative analysis of other fluid constituents occurring during respiration.

OBJECT AND SUMMARY OF THE INVENTION

It is therefore an object of the present invention to provide a method and apparatus for measurement of respiratory fluid constituents by indirect means, thereby avoiding expensive and complicated detection/measurement systems.

It is a further object of the present invention to provide means for determining the rate of $CO_2$ production during respiration.

It is a further object of the subject invention to provide a method and apparatus for determination of metabolic rate of a living subject.

It is yet another object of the invention to develop an absorption-titration technique for the identification and measurement of selected fluid constituents in expired air.

A still further object of this invention is to adapt such a method for application to special monitoring situations, including neonatal intensive care units and intensive care units in general.

These and other inventive objects are realized in an apparatus for determining the amount of a selected fluid constituent expired by a living subject during respiration. Such apparatus includes a fluid path with means coupled within the confined volume to measure concentration or other quantative parameters for the given fluid. Subsequent to such measurement, the expired air is subjected to means for removing the fluid constituent, thereafter passing the expired air to a mixing chamber for exposure to a second detection means which is likewise sensitive to concentration of the fluid constituent. Also coupled to the mixing chamber is a metering device which provides controlled introduction of the fluid to the originally detected concentration level. Such replenishment occurs by the metered addition of the fluid at the mixing chamber until fluid concentrations monitored by the respective first and second detection means are equivalent. The rate of expiration of original fluid constituent is determined from the fluid addition flow rate required to obtain a null difference between signals from the respective detection means.

This apparatus and method may be coupled with systems for measuring oxygen consumption to thereby provide the important combined parameters of $\dot{V}O_2$ and $\dot{V}CO_2$. Other fluid constituents associated with respiration or respiratory gases can be implemented by the same method. Because this method does not require direct quantitative measurement, it has considerable advantage in terms of simplicity and expense.

Other objects and features of the present invention will be apparent to those skilled in the art, in view of the following detailed description, taken in combination with the attached drawings.

DETAILED DESCRIPTION OF THE DRAWINGS

Figure 1:
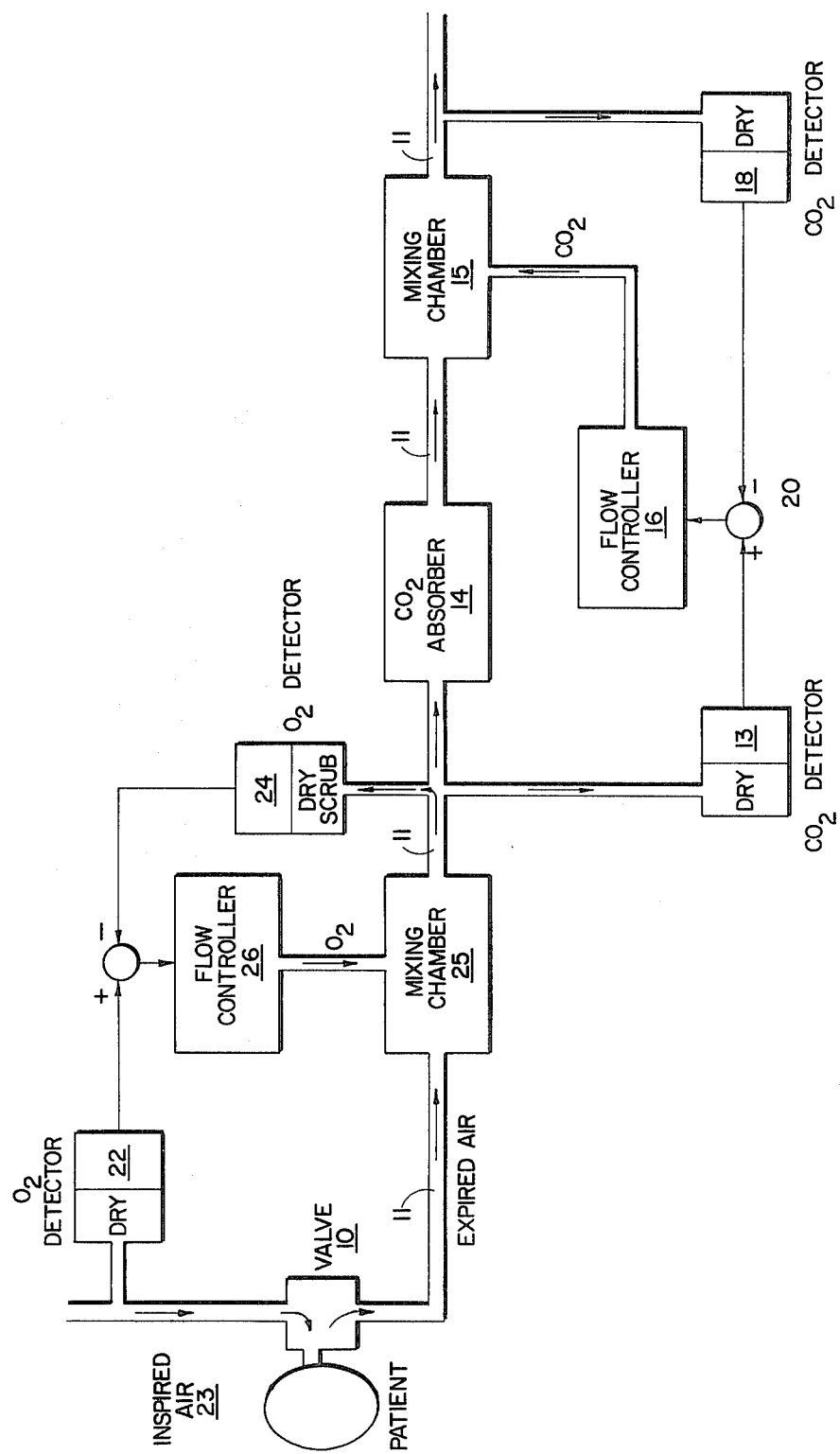

FIG. 1 shows a blocked diagram of the subject invention as applied to $CO_2$, in combination with an oxiconsumeter for $O_2$ measurement.

Figure 2:
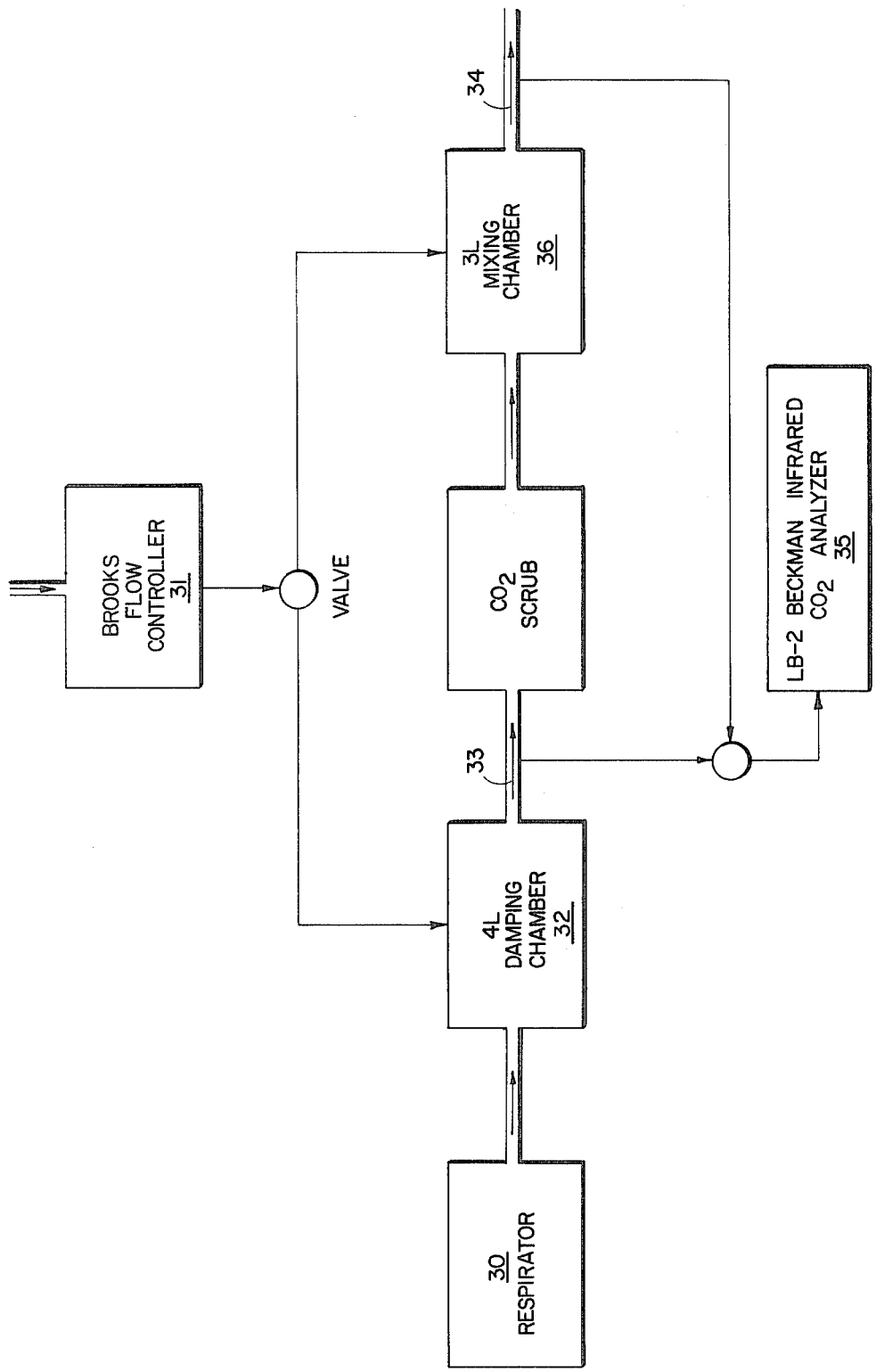

FIG. 2 discloses a flow chart representing function parts of an actual experimental embodiment of a $CO_2$ measurement device.

DETAILED DESCRIPTION OF THE INVENTION

Referring now to the drawings:

In a generic sense, the subject invention comprises a dynamic or continuing absorption-titration technique for measuring the flow rate of a selected fluid constituent in expired air by a living subject during respiration. Implementation of this process to a given fluid involves the steps of exposing a sample fraction of the expired air to a detection means producing a first signal which is a function of concentration of the selected fluid constituent. Such sensitivity may be in terms of partial pressure of the subject fluid or any other characteristic which permits the relative comparison of concentration of the same fluid in different environments. This signal representating the relative concentration of the selected fluid first measured is retained or delayed for subsequent use. The expired air is then subjected to a step in which substantially all of the fluid constituent is removed. Alternatively, the fluid can be partially removed, provided the percent of depletion is determined so that subsequent replenishment techniques may be used to calculate or adjust the expiration rate to the original fluid constituent flow rate.

With all or a known percent of the selected fluid removed from the expired air sample, a metering pump is used to replenish the expired air to the original level of fluid concentration. Such replenishment is accomplished by detection means which are sensitive to the fluid concentration as fluid is added by the metering pump. When a null signal is obtained between the respective detection means, the fluid addition flow rate can be used as a base to determine the fluid expiration rate in the expired air.

As an example of the application of this invention to a given fluid constituent, FIG. 1 shows such an apparatus useful for determining the value of $\dot{V}CO_2$. A patient is illustrated at the left of the figure with a valve 10 or other means for coupling the subject apparatus directly to a living subject to provide continuous withdrawal of expired air. Such expired air is directed along a fluid path 11 or similar means for containing the expired air within a confined volume. This expired air is exposed to a first detection means 13 providing a signal representing concentration of $CO_2$.

Any $CO_2$ detector which is sensitive to a concentration may be utilized as a detector means for the subject invention. An exemplary inexpensive gas chromatographic $CO_2$ detector can be constructed of two independent channels providing comparison of a known $CO_2$ reference concentration and $CO_2$ fluid sample for measurement. The channels may be formed as bored openings in a metal block, each containing matched thermistors as the detection means which function in response to exposed $CO_2$ concentration. The pair of thermistors operate as two arms of a Wheatstone bridge which is biased with sufficient voltage to cause the thermistor to self-heat.

A dry sample fraction of $CO_2$ containing fluid to be measured is introduced at the measurement channel and compared with the known reference by virtue to a difference of thermal conductivity which occurs between $CO_2$ and other constituents of the respiratory fluid exposed at the thermistor. This difference causes an imbalance in the bridge circuit which responds as a function of fluid sample $CO_2$ concentration relative to the $CO_2$ reference channel fluid. Other methods for $CO_2$ detection include spectrophotometry, paramagnetism, mass spectroscopy and techniques of analytical chemistry.

The expired air next passes as a $CO_2$ absorber 14 which scrubs the air of $CO_2$ constituent. Inasmuch as the subject invention provides a replenishment technique for determining quantative analysis, the absorption step is a significant requirement of such an apparatus. It will be apparent, therefore, that application of the subject invention to any selected fluid constituent would require that means exist for removal of part of or all of such fluid constituent. In the case of partial removal, it will be necessary to at least determine what percentage of fluid has been removed so that subsequent calculations can adjust the measured fluid flow rate upward to correspond to the fluid flow actually occurring in the initial expired air.

Subsequent to removal of the fluid constituent, the expired air continues along the fluid path 11 to a mixing chamber 15. In the subject embodiment, the replenishment metering device 16 is coupled to the mixing chamber to provide controlled flow of $CO_2$ into the expired air. The rate of $CO_2$ addition is controlled by a second detection means 18 which monitors $CO_2$ flow rate in the flow channel 11 immediately following the mixing chamber 15.

A regulating means 20 compares the respective signals of the first detection means 13 and the second detection means 18 and drives the metering device 16 until such signals equalize. When the signal of the second detection means 18 reaches the value of the signal of the first detection means 13, fluid flow rates have been normalized and determination of actual rate of fluid expiration can be accomplished. A dynamic response for replenishment is developed by integrating the difference registered between the respective detection means 13 and 18 with previously recorded differences.

As stated previously, the advantage of the subject system over prior art device includes the avoidance of direct measurement of fluid concentration. Instead, a relative concentration parameter, such as $pCO_2$ can be determined for pre and post-absorption stages of the method. Replenishment of $CO_2$ is simply effected until the respective values of $pCO_2$ fo the pre and post-absorption stages are equivalent. This method thereby avoids the previously required determination of a patient's exhaled flow or volume, along with the other parameters required to make direct quantative analysis.

It is preferred that the determination of $\dot{V}CO_2$ be made during steady-state conditions of a patient in order that the flow rate of $CO_2$ exhaled from the lungs in equal to the $CO_2$ produced by the body cells. Normally, acid-base changes within the body are buffered by proteins, hemoglobin, phosphates and $HCO_3^-$, and later being developed in accordance with the following reaction:

$$CO_2 + H_2O \rightleftharpoons H_2CO_3^- + H^+ + HCO_3^-$$

It can be seen from this expression that $CO_2$ may be produced by the cells and then subsequently buffered to form $HCO_3^-$, rather than being voided from the body by expiration. Obviously, such consumption of $CO_2$ in the buffering process will decrease the accuracy of the relative measurement accomplished by the subject process. When the minute ventilation is suddenly doubled the arterio-$pCO_2$ is immediately halved as $CO_2$ fluid is blown off by the lungs. When ventilation returns to normal the arterial-$pCO_2$ returns exponentially at a rate dependent upon the celular $CO_2$ production rate. It therefore becomes important that $\dot{V}CO_2$ be measured during steady-state conditions when acute changes in ventilation and acid-base balance are not present.

Knowledge of the values for $\dot{V}CO_2$ are particularly significant when combined with values for $\dot{V}O_2$. The embodiment illustrated in FIG. 1 also discloses an oxiconsumeter coupled to the subject measurement system. The oxiconsumeter segment of the overall system of FIG. 1 requires an $O_2$ detector 22 which samples the oxygen level contained in the inspired air 23 taken in by the patient. The rate of oxygen consumed during respiration is determined by comparing this first measurement with a signal from a comparable $O_2$ detector 24 which monitors oxygen replenishment at a preceding mixing chamber 25. Oxygen replenishment is regulated by a flow controller 26 which responds to the signals from the first and second oxygen detectors 22 and 24. The rate of oxygen consumption by the patient is determined by the rate of resupply required to replenish the expired air to it's original oxygen concentration.

Knowledge of the values for $\dot{V}O_2$ and $\dot{V}CO_2$ permit a determination of RQ, the respiratory quotient ($\dot{V}CO_2/\dot{V}O_2$), which can be enlightening as to numerous body functions related to metabolism and nutrition. Such parameters can be coordinated with known quantities of protein, fat and water contribution to body weight changes and can thereby be employed to develop appropriate nutrition plans. These additional protein fat parameters can be obtained using conventional and indirect calorimetry by measuring the uptake of oxygen, the output of carbon dioxide and the excretion of nitrogen with respect to each type of food stuff metabolized. Any oxygen and carbon dioxide involved in the protein metabolism can be subtracted from the totals, leaving the preferred non-protein rates of oxygen consumption ($\dot{V}O_2$) and carbon dioxide production ($\dot{V}CO_2$).

Other areas of application of the subject method and apparatus include management of a neonate's alimentation relative to the thermo-environment. A knowledge of $\dot{V}O_2$ and $\dot{V}CO_2$ and RQ provide an assessment of the neonate's nutritional status. With respect to thermo-environment, it is extremely important in newborn intensive care units that such environments be maintained at a temperature which minimizes metabolic requirements. On line, continuous measurements of $\dot{V}O_2$, $\dot{V}CO_2$ and RQ will allow rapid feedback in regulating such a thermo-environment for the neonate.

Actual experimental results have confirmed the utility and accuracy of the subject apparatus and are illustrated in Table 1 below.

TABLE 1

$\dot{V}CO_2$ simulation experiment.

| Controlled $\dot{V}CO_2$ (cc $CO_2$/min) | Prototype $\dot{V}CO_2$ (cc $CO_2$/min) | Percent difference |
|---|---|---|
| 20.40 | 22.53 | 10.44 |
| 34.00 | 35.70 | 5.00 |
| 56.95 | 57.80 | 1.49 |
| 61.20 | 63.75 | 4.17 |
| 77.35 | 79.05 | 2.20 |
| 81.60 | 87.55 | 7.29 |
| 93.50 | 95.20 | 1.82 |
| 95.20 | 96.90 | 1.79 |
| 108.80 | 113.05 | 3.91 |
| 115.60 | 119.85 | 3.68 |
| 118.15 | 118.15 | 0.00 |
| 132.60 | 136.85 | 3.21 |
| 140.25 | 141.95 | 1.21 |
| 141.95 | 146.20 | 2.99 |
| 157.25 | 158.10 | 0.54 |
| 170.85 | 171.70 | 0.50 |
| 170.85 | 174.25 | 1.99 |
| 191.25 | 199.75 | 4.44 |
| 195.50 | 203.15 | 3.91 |
| 209.10 | 217.60 | 4.07 |
| 233.75 | 240.55 | 2.91 |

The particular system used was that illustrated in FIG. 2. The respirator 30 was set to deliver room air at 500 ml. per breath and at a rate at 10 breaths per minute. A controlled flow of $CO_2$ was actuated by a Brooks flow controller 31 and added to the four liter mixing chamber 32 at rates varing from 25 to 250 ml per minute. The $CO_2$ fraction was monitored a 0.33 and 0.34 by an LB-2 Beckman infrared $CO_2$ analyzer 35.

Next, with respirator settings unchanged, the output of the Brooks controller 31 was directed into the three liter mixing chamber 36, with the $CO_2$ fraction at the output being monitored by the $CO_2$ analyzer 35. The flow controller 31 was adjusted to give $CO_2$ readings at 0.34 identical to those previously recorded at 0.33. These results are indicated in Table 1 above. The average percent difference between the controlled $\dot{V}CO_2$ and the prototype's $\dot{V}CO_2$ measurements was 3.22% with a standard deviation of 2.4. Correlation coefficient was 0.99944. Aside from some error attributable to connection leaks, the prototype system confirms the utility of the subject method and a apparatus.

Calculations for the $CO_2$ or other selected fluids to be measured can best be effected by a small computer or microcomputer. Computer design and programming are well within the state of the art to perform the functions required by the subject apparatus. Critical functions to be implemented in such a computer include the I/O routine for determining the sampling rate for the concentration centers, processing the calculations, and encoding the data appropriately for the flow controllers and various displays. Compensation functions will also be necessary and may be implemented by using a set of difference equations specifically optimized with respect to a particular system designed.

Construction of the subject apparatus can be of numerous materials and designs. Chambers may consist of plexiglass with copper for heat dissipation arising from the $CO_2$ scrubbing agent. Silica-gel can be used to dry the gas samples prior to exposure at the detection means. The system can be coupled to a patient by means of a conventional mask or in conjunction with any standard ventilator.

In addition to the applications of the subject apparatus and method for measurement of $\dot{V}CO_2$ and metabolism, other respiratory fluids can be monitored, provided an absorption means is available to extract such fluids from the expired air. Anesthetic vapors, for example, could be measured before post-operative washout to determine extended perfusion and other related matters of interest. Likewise, substances which are injected in the blood and subsequently expired through the lungs can be measurd effectively with the subject apparatus. Xenon or helium expiration could be used, for example, to determine partition coefficients of lung membranes. Similarly, water vapor production could be measured in accordance with the disclosed method. The subject invention is also adaptable for nonclinical applications, such as measurements of blood-alcohol content by law enforcement personnel.

Although preferred forms of the invention have been herein described, it is to be understood that the present disclosure is by way of example and that variations are possible without departing from the scope of the hereinafter claimed subject matter, which subject matter, which subject matter is to be regarded as the invention.

We claim:

1. A dynamic method for determining rate of expiration of a selected fluid constituent in a mixed flow of expired respiration fluids, comprising the recurring steps of:

a. exposing a first sample fraction of the expired fluids to detection means producing a first signal which is a function of concentration of said selected fluid constituent, b. removing substantially all of said fluid constituent from a second fraction of the expired fluids, c. exposing said second fraction to detection means producing a second signal which is a function of concentration of the selected fluid constituent, d. comparing said first and second signals, e. replenishing said second fraction of expired fluids with resupply of said fluid constituent at a sufficient flow rate to equalize the compared signals of the previous step, and f. monitoring the flow rate to provide data for determining said rate of expiration.

2. A dynamic method for determining rate of expiration of a selected fluid constituent in a mixed flow of expired respiration fluids, comprising the recurring steps of:

a. monitoring concentration of said selected fluid constituent in the expired respiration fluids, b. removing a known portion of said monitored fluid constituent from the expired respection fluids, c. replenishing the expired fluids of step b with said fluid constituent by controlled metering thereof in response to detection and regulation means which compare and equalize fluid concentration of the replenished respiration fluids with the fluid concentration of step a and integrate differences registered between the detection means to provide a dynamic response for replenishment in accordance with previously detected differences in concentration, d. monitoring flow rate of said control metering device to provide data for determining rate of expiration, and e. adjusting the value of step d upward by a factor based on the known portion of fluid removed under step b to thereby determine correct value for rate of expiration of said fluid originally present in the expired fluids.

3. A method as defined in claim 1 or 2 further comprising the step of replenishing the expired fluids until a null reading is obtained between the detection means.

4. A method as defined in claim 1 or 2 wherein said replenishment step is accomplished by means of a servo-controlled flow pump which meters fluid input into the expired fluids in response to a voltage differential representing variation between said fluid concentrations being compared.

5. A method as defined in claim 1 or 2, wherein said fluid constituent comprises $CO_2$.

6. A method as defined in claim 5 wherein the removel step comprises absorption of said $CO_2$.

7. A method as defined in claim 5, wherein said detection means are sensitive to partial pressure ($pCO_2$) of the fluid constituent.

8. A method as defined in claim 5 further comprising the step of determining $CO_2$ production rate ($\dot{V}CO_2$) of a living subject by (a) applying said method to fluids expired by the living subject during respiration and (b) correlating rate of replenishment of $CO_2$ absorbed from the expired fluids with known system parameters to obtain a value for $CO_2$ produced by the subject.

9. A method as defined in claim 8, further comprising the steps of measuring oxygen consumption rate ($\dot{V}O_2$) of said expiration fluids.

10. A method as defined in claim 9, wherein $\dot{V}O_2$ is obtained by an oxiconsumeter system coupled to a fluid path apparatus utilized for determining $\dot{V}CO_2$.

11. A method as defined in claim 1, wherein the fluid constituent is selected from the group consisting of (a) fluid anesthetics, including halothane, ethrane, penthrane, ether and $N_2O$, (b) xenon, (c) cyclopropane, (d) alcohols, (e) helium, and (f) water vapor.

12. Apparatus for determining rate of expiration of a selected fluid constituent in a mixed flow of expired respiration fluids, comprising:

a. means for containing said expired air within a confined volume, b. first detection means coupled to said confined volume for producing a first signal which is a function of concentration of said fluid constituent, c. means for removing said fluid constituent from a fraction of the contained expired fluids, d. a mixing chamber coupled to receive said fluids having said fluid constituent removed, e. second detection means coupled to said mixing chamber for producing a second signal which is a function of concentration of said fluid constituent, f. metering means to provide controlled introduction for resupply of said fluid constituent to said mixing chamber, g. regulating means for comparing signals from the first and second detection means and for driving said metering means to resupply fluid constituent at a flow rate sufficient to obtain a null difference in signal obtained, and h. means for monitoring said flow rate to provide data relating to said rate of expiration.

13. Apparatus as defined in claim 12, further comprising means for coupling said confined volume directly to a living subject to continuously receive expired fluids during respiration, thereby adapting said apparatus for recurring, dynamic measurement of rate of expiration for a selected fluid constituent.

14. Apparatus as defined in claim 12, wherein
said removing means comprise a $CO_2$ absorber coupled between said confined volume and said mixing chamber, and said detector means comprise $CO_2$ sensitive detectors.

15. Apparatus as defined in claim 14 further comprising oxiconsumeter means coupled with said apparatus for measuring and computing oxygen consumption rate ($\dot{V}O_2$) of said living subject.

16. Apparatus as defined in claim 12, wherein the removing means comprise means for removing fluids selected from the group consisting of (a) fluid anesthetics, including halothane, ethrane, penthrane, ether and $N_2O$, (b) xenon, (c) cyclopropane, (d) alcohols, (e) helium, and (f) water vapor.

* * * * *